(12) United States Patent
Lee et al.

(10) Patent No.: US 12,343,441 B2
(45) Date of Patent: Jul. 1, 2025

(54) STERILIZATION UNIT AND STERILIZATION APPARATUS INCLUDING THE SAME

(71) Applicant: SEOUL VIOSYS CO., LTD., Ansan-si (KR)

(72) Inventors: Chung Hoon Lee, Ansan-si (KR); Ji Won Kim, Ansan-si (KR); Jae Hak Jeong, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 0 days.

(21) Appl. No.: 18/739,605

(22) Filed: Jun. 11, 2024

(65) Prior Publication Data

US 2024/0325579 A1 Oct. 3, 2024

Related U.S. Application Data

(63) Continuation of application No. 17/335,785, filed on Jun. 1, 2021, now Pat. No. 12,070,524.

(60) Provisional application No. 63/064,491, filed on Aug. 12, 2020, provisional application No. 63/033,386, filed on Jun. 2, 2020.

(51) Int. Cl.
*A61L 2/10* (2006.01)

(52) U.S. Cl.
CPC ............. *A61L 2/10* (2013.01); *A61L 2202/11* (2013.01); *A61L 2202/14* (2013.01); *A61L 2202/16* (2013.01); *A61L 2202/25* (2013.01)

(58) Field of Classification Search
CPC .... A61L 2/10; A61L 2202/11; A61L 2202/14; A61L 2202/16; A61L 2202/25
USPC .............. 250/453.11, 454.11, 455.11
See application file for complete search history.

(56) References Cited

U.S. PATENT DOCUMENTS

| 12,070,524 B2 * | 8/2024 | Lee ..................... A61L 9/20 |
| 2018/0193499 A1 | 7/2018 | Lu et al. |
| 2018/0256764 A1 | 9/2018 | Kreitenberg |
| 2021/0077651 A1 | 3/2021 | Romo et al. |
| 2021/0369894 A1 | 12/2021 | Lee et al. |

FOREIGN PATENT DOCUMENTS

| EP | 3316915 B1 | 11/2019 |
| EP | 3592394 A1 | 1/2020 |
| JP | 06063107 A | 3/1994 |
| JP | 2020511344 A | 4/2020 |
| KR | 101724481 B1 | 4/2017 |
| KR | 101742489 A1 | 6/2017 |
| KR | 101742489 B1 | 6/2017 |
| WO | 2014038897 A1 | 3/2014 |
| WO | 2014100493 A1 | 6/2014 |
| WO | 2018164845 A1 | 9/2018 |
| WO | 2019143699 A1 | 7/2019 |

OTHER PUBLICATIONS

International Search Report for corresponding International Application No. PCT/KR2021/006867, mailed Sep. 14, 2021.
European Search Report for European Patent Application EP 2187798, dated Apr. 19, 2024 (11 pages).
Office Action from corresponding related Chinese Patent Application No. 202180040114.7, dated Mar. 29, 2025.

* cited by examiner

*Primary Examiner* — Nicole M Ippolito
(74) *Attorney, Agent, or Firm* — Perkins Coie LLP

(57) ABSTRACT

Disclosed herein are a sterilization module and a sterilization apparatus including the same. The sterilization module includes a support member and multiple germicidal light sources. The multiple germicidal light sources are mounted on the support member and emit germicidal light which is light having a wavelength capable of inactivating microorganisms. In addition, respective light exit surfaces of the multiple germicidal light sources face in different directions from one another. Further, an irradiance of the germicidal light delivered to a sterilization target is greater than a minimum irradiance required for sterilization.

20 Claims, 15 Drawing Sheets

STERILIZATION UNIT AND STERILIZATION APPARATUS INCLUDING THE SAME

CROSS-REFERENCE TO RELATED APPLICATIONS

This present application is a continuation of U.S. patent application Ser. No. 17/335,785, dated Jun. 1, 2021, which claims priority to and the benefit of U.S. Provisional Application No. 63/033,386 filed Jun. 2, 2020, and U.S. Provisional Application No. 63/064,491 filed Aug. 12, 2020. The aforementioned applications of which are incorporated herein by reference in their entireties.

TECHNICAL FIELD

Embodiments of the present disclosure relate to a sterilization unit and a sterilization apparatus including the same.

BACKGROUND

Recently, with spread of viruses that threaten human health, such as COVID-19, efforts are being made to kill the viruses to protect humans from infection.

In particular, a sterilization luminaire capable of sterilizing a living space, such as a house and an office, has recently been in the spotlight.

However, such a sterilization luminaire is generally a built-in product, which is not portable from space to space. Accordingly, many built-in sterilization luminaires are needed to sterilize each space, thus resulting in increased expenses.

Further, a general portable sterilization device is intended to sterilize a specific object with germicidal light and thus provides a small range of illumination. Accordingly, such a portable sterilization device is not suitable for sterilizing the entire region of a living space such as a house and an office.

The above information disclosed in this Background section is only for understanding of the background of the inventive concepts, and, therefore, it may contain information that does not constitute prior art.

SUMMARY

Embodiments of the present disclosure provide a sterilization module which can sterilize a space, and a sterilization apparatus including the same.

Embodiments of the present disclosure provide a sterilization module which can uniformly deliver germicidal light throughout a space to be sterilized, and a sterilization apparatus including the same.

Embodiments of the present disclosure provide a sterilization apparatus which can be easily moved from space to space as necessary.

Embodiments of the present disclosure provide a sterilization apparatus which can automatically control a sterilization operation.

In accordance with one aspect of the present disclosure, there is provided a sterilization module including a support member and multiple germicidal light sources. The multiple germicidal light sources are mounted on the support member and emit germicidal light, which is light having a wavelength capable of inactivating microorganisms. Respective light exit surfaces of the multiple germicidal light sources face in different directions from one another. The sterilization module illuminates a sterilization target with the germicidal light at an irradiance greater than a minimum irradiance required for sterilization.

The sterilization unit may include a first sterilization unit and a second sterilization unit each comprising a support member and multiple germicidal light sources. In addition, the first sterilization unit and the second sterilization unit may face in different directions from one another.

The sterilization unit may include a pair of first sterilization units spaced apart from each other and facing in opposite directions and a pair of second sterilization units spaced apart from each other and facing in opposite directions. The pair of second sterilization units may be disposed between the pair of first sterilization units.

The sterilization unit may further include a third sterilization unit comprising germicidal light sources. Here, the third sterilization unit may be disposed between the first sterilization unit and the second sterilization unit.

Alternatively, the third sterilization unit may be disposed above or below the first sterilization unit or the second sterilization unit.

Respective light exit surfaces of two germicidal light sources disposed at opposite ends of the support member, among the multiple germicidal light sources, may face in opposite directions with respect to a central axis of the support member.

The sterilization unit may further include multiple securing members each having a mounting surface on which the germicidal light source is mounted. Here, respective mounting surfaces of the multiple securing members may face in different directions from one another.

The sterilization module has an illumination uniformity of 75% or more.

In accordance with another aspect of the present disclosure, a sterilization apparatus includes a main frame, a sterilization unit, and multiple connection members. The sterilization unit includes multiple germicidal light sources emitting germicidal light, which is light having a wavelength capable of inactivating microorganisms. The multiple connection members connect the main frame to the sterilization unit. The sterilization unit includes a first sterilization unit and a second sterilization unit each including a support member and multiple germicidal light sources. The multiple germicidal light sources are disposed on the support member with respective light exit surfaces thereof facing in different directions from one another. The sterilization apparatus illuminates a sterilization target with the germicidal light at an irradiance greater than a minimum irradiance required for sterilization.

The first sterilization unit and the second sterilization unit may face in different directions from one another.

The sterilization unit may include a pair of first sterilization units spaced apart from each other and facing in opposite directions and a pair of second sterilization units spaced apart from each other and facing in opposite directions. Here, the pair of second sterilization units may be disposed between the pair of first sterilization units.

The sterilization unit may further include a third sterilization unit including germicidal light sources and mounted on the connection member or the main frame. Here, the third sterilization unit may be disposed between the first sterilization unit and the second sterilization unit.

Alternatively, the third sterilization unit may be disposed above or below the first sterilization unit or the second sterilization unit.

Respective light exit surfaces of two germicidal light sources disposed at opposite ends of the support member, among the multiple germicidal light sources, may face in opposite directions with respect to a central axis of the support member.

The sterilization unit may further include multiple securing members each having a mounting surface on which the germicidal light source is mounted and a securing portion secured to the support member. Here, respective mounting surfaces of the multiple securing members may face in different directions from one another.

The sterilization apparatus may further include an object detection sensor detecting movement of an object.

The sterilization apparatus may further include a controller controlling the sterilization unit to stop emission of the germicidal light upon detection of an object by the object detection sensor.

The sterilization apparatus may further include at least one of a distance sensor measuring a distance to a sterilization target and a timer transmitting a signal for controlling sterilization time to the controller.

The sterilization apparatus may further include a calculation unit calculating at least one of intensity of the germicidal light and sterilization time based on at least one of information about the distance to the sterilization target and information about the sterilization time.

The sterilization apparatus has an illumination uniformity of 75% or more.

In accordance with some embodiments of the present disclosure, the sterilization module and the sterilization apparatus can uniformly deliver germicidal light throughout a space to be sterilized, thereby providing improved sterilization efficiency.

In accordance with other embodiments of the present disclosure, the sterilization apparatus can be moved from space to space. Thus, unlike conventional built-in sterilization apparatuses, the sterilization apparatus according to the present disclosure can eliminate the need to install one sterilization apparatus in each space, thereby providing cost saving benefits.

In accordance with yet other embodiments of the present disclosure, the sterilization apparatus can perform efficient sterilization through automatic calculation of sterilization conditions depending on the type of spaces to be sterilized.

It is to be understood that both the foregoing general description and the following detailed description are exemplary and explanatory and are intended to provide further explanation of the disclosure as claimed.

BRIEF DESCRIPTION OF THE DRAWINGS

The accompanying drawings, which are included to provide a further understanding of the disclosure and are incorporated in and constitute a part of this specification, illustrate exemplary embodiments of the disclosure, and together with the description serve to explain the inventive concepts.

FIG. 1 illustrates a perspective view of a sterilization apparatus;

FIG. 2 illustrates a side view of the sterilization apparatus of FIG. 1; and

FIG. 3 illustrates the sterilization apparatus of FIG. 1 in which sterilization units are coupled to the main frame.

FIG. 5 is a perspective view of the sterilization apparatus according to the third embodiment; and FIG. 6 is a side view of the sterilization apparatus according to the third embodiment.

FIG. 8 is a perspective view of the sterilization apparatus; and

FIG. 9 illustrates a first mounting surface tiled at a predetermined angle.

FIG. 10A shows the light distribution of the sterilization apparatus according to the fourth embodiment;

FIG. 10B shows the light distribution of the sterilization apparatus according to the fourth embodiment around the center of a space to be sterilized; and FIG. 10C shows the light distribution of the conventional sterilization apparatus.

FIG. 12 illustrates a main frame having a cuboidal shape; and

FIG. 13 illustrates an additional sterilization unit disposed on each surface of the main frame of FIG. 12.

DETAILED DESCRIPTION

Figure 1:
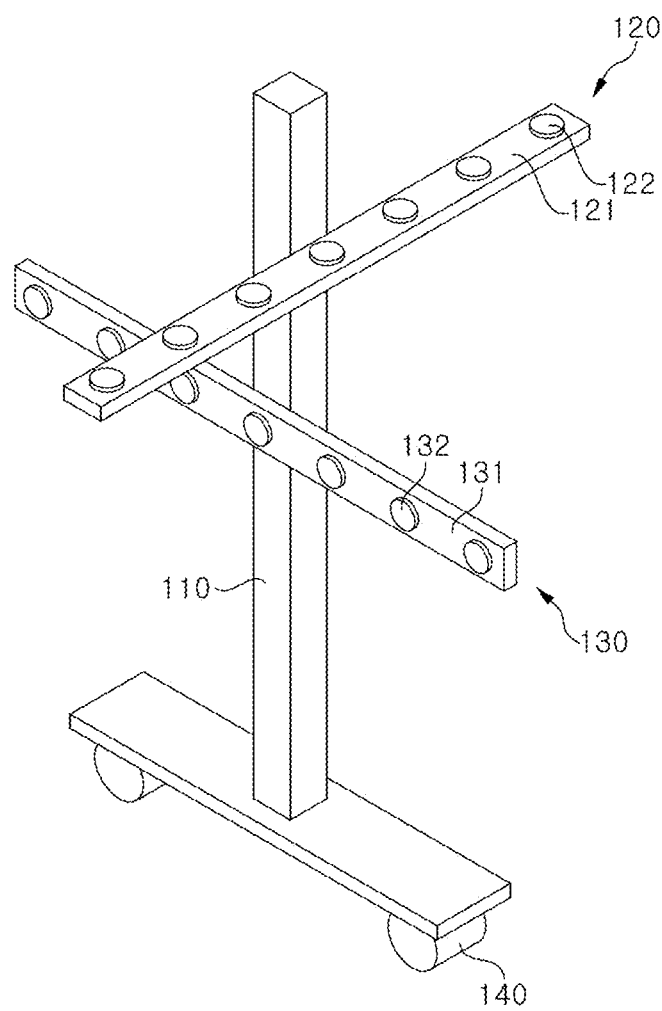
FIG. 1 to FIG. 3 are exemplary views of a sterilization apparatus according to a first embodiment of the present disclosure, where.

Hereinafter, embodiments of the present disclosure will be described with reference to the accompanying drawings. It should be understood that the embodiments are provided for complete disclosure and a thorough understanding of the present disclosure by those skilled in the art. Therefore, the present disclosure is not limited to the following embodiments and may be embodied in different ways. In addition, the drawings may be exaggerated in width, length, and thickness of components for descriptive convenience and clarity only. Like components will be denoted by like reference numerals throughout the specification.

Figure 2:
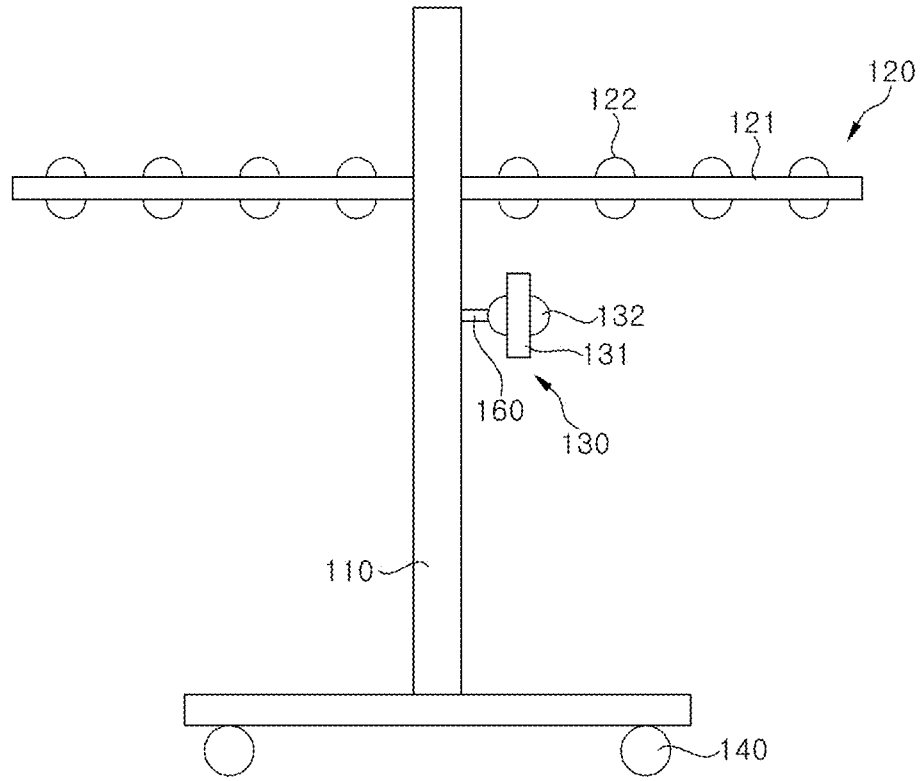
Figure 3:
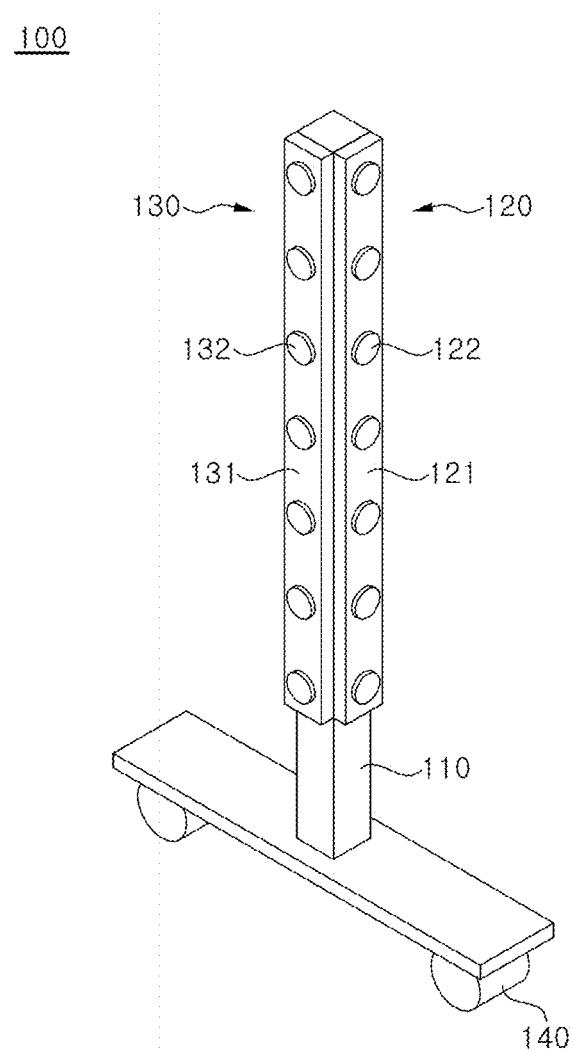

FIG. 1 to FIG. 3 are exemplary views of a sterilization apparatus according to a first embodiment of the present disclosure.

FIG. 1 is a perspective view of the sterilization apparatus 100 according to the first embodiment of the present disclosure. FIG. 2 is a side view of the sterilization apparatus 100 according to the first embodiment of the present disclosure.

Referring to FIG. 1 and FIG. 2, the sterilization apparatus 100 according to the first embodiment includes a main frame 110 and a sterilization unit.

The main frame 110 extends in a vertical direction.

In addition, the main frame 110 supports the sterilization unit with a space between the sterilization unit and the floor. In this way, the main frame 110 allows germicidal light emitted from the sterilization unit to be efficiently delivered to a sterilization target. Here, the sterilization target may be a specific object. Alternatively, the sterilization target may be a space in which the sterilization apparatus 100 is located.

The main frame 110 may have a vertically elongated shape.

The sterilization apparatus 100 may include multiple sterilization units. The multiple sterilization units may be mounted on the main frame 110.

Each of the multiple sterilization units includes a support member and a germicidal light source mounted on the support member. The germicidal light source may be, for example, a light emitting diode chip or a light emitting diode package.

The support member has an elongated shape and is secured to the main frame 110. The support member is horizontally secured to the main frame 110.

The support member is adapted to horizontally arrange multiple germicidal light sources thereon and may be formed of any material that can support the multiple germicidal light sources.

In one embodiment, the support member may be a substrate with a circuit pattern formed thereon. In this embodiment, power can be supplied to the multiple germicidal light sources through the circuit pattern of the support member.

In another embodiment in which the support member is not formed with a circuit pattern, a separate substrate or cable may be mounted on the support member to supply power to the germicidal light sources therethrough.

At least one of the multiple support members may be positioned non-parallel to the other support members.

Referring to FIG. 1, the sterilization unit may include a first sterilization unit 120 and a second sterilization unit 130. Although the sterilization unit is described as including the first sterilization unit 120 and the second sterilization unit 130, the first sterilization unit 120 and the second sterilization unit 130 are different as respective support members of the sterilization units face in different directions from each other.

Accordingly, characteristics of one of the first sterilization unit 120 and the second sterilization unit 130 can be equally applied to the other one.

The first sterilization unit 120 may include a first support member 121 and multiple first germicidal light sources 122, and the second sterilization unit 130 may include a second support member 131 and multiple second germicidal light sources 132. As described above, the first support member 121 and the second support member 131 may be identical to each other except that the first support member 121 and the second support member 131 face in different directions from each other.

In addition, the first germicidal light source 122 and the second germicidal light source 132 may be identical to each other. In brief, a germicidal light source mounted on the first support member 121 is referred to as the first germicidal light source 122, and a germicidal light source mounted on the second support member 131 is referred to as the second germicidal light source 132.

Both the first support member 121 and the second support member 131 may be horizontally secured to the main frame 110.

Here, the first support member 121 and the second support member 131 may disposed to cross each other.

The germicidal light source emits germicidal light to sterilize a sterilization target. The germicidal light may be any wavelength of light that can inactivate microorganisms. For example, the germicidal light may be light having germicidal power, such as blue light and UV light. In particular, UVC is known to have high germicidal capability.

The sterilization apparatus 100 according to this embodiment illuminates a sterilization target with the germicidal light at an intensity greater than or equal to a minimum intensity required for sterilization.

Referring to FIG. 1, the first germicidal light source 122 may be mounted on both surfaces of the first support member 121, and the second germicidal light source 132 may be mounted on both surfaces of the second support member 131.

The first support member 121 may be disposed such that the opposite surfaces thereof having the respective first germicidal light sources 122 mounted thereon face in upward and downward directions of the main frame 110, respectively. That is, one side surface of the first support member 121, which is connected between the opposite surfaces having the respective first germicidal light sources 122 mounted thereon, may be secured to the main frame 110.

The second support member 131 may be disposed such that the opposite surfaces thereof having the respective second germicidal light sources 122 mounted thereon face in opposite lateral directions of the main frame 110, respectively. That is, one of the opposite surfaces of the second support member 131 having the respective second germicidal light sources 122 mounted thereon may be partially secured to the main frame 110.

Each of the first sterilization unit 120 and the second sterilization unit 130 may include a connection member 160.

The connection member 160 of the first sterilization unit 120 may connect the first support member 121 to the main frame 110. In addition, the connection member 160 of the second sterilization unit 130 may connect the second support member 131 to the main frame 110. That is, the connection member 160 of the first sterilization unit 120 is connected at one end thereof to the main frame 110 and is connected at the other end thereof to the first support member 121. In addition, the connection member 160 of the second sterilization unit 130 is connected at one end thereof to the main frame 110 and is connected at the other end thereof to the second support member 131.

The connection member 160 of the second sterilization unit 130 may allow the main frame 110 to be spaced apart from the second support member 131, as shown in FIG. 2. In addition, although not shown, the connection member 160 of the first sterilization unit 120 may allow the main frame 110 to be spaced apart from the second support member 131.

In addition, the sterilization apparatus 100 according to this embodiment may change a travel direction of the germicidal light through adjustment of angles of the first sterilization unit 120 and the second sterilization unit 130.

For example, each of the first sterilization unit 120 and the second sterilization unit 130 is adjustable in angle with respect to a longitudinal direction of the main frame 110. In addition, each of the first sterilization unit 120 and the second sterilization unit 130 is movable along a side periphery of the main frame.

In addition, each of the first sterilization unit 120 and the second sterilization unit 130 is pivotally coupled to the main frame 110. In this way, the sterilization apparatus 100 can be carried in compact form with the first sterilization unit 120 and the second sterilization unit 130 pivoted to be parallel to the main frame 110, as shown in FIG. 3.

Adjustment of the angles of the first sterilization unit 120 and the second sterilization unit 130 may be performed through the first support member 121 and the second support member 131 or through the connection member 160.

In addition, adjustment of the angles of the first sterilization unit 120 and the second sterilization unit 130 may be implemented by any angle adjustment technique known in the art, without limitation.

Through adjustment of the angles of the first sterilization unit 120 and the second sterilization unit 130, the sterilization apparatus according to this embodiment can provide efficient sterilization regardless of the location of a sterilization target. In addition, the sterilization apparatus according to this embodiment can provide efficient sterilization through adjustment of the angles of the first sterilization unit 120 and the second sterilization unit 130 depending on the shape of a space to be sterilized.

With the first support member 121 and the second support member 131 secured to the main frame 110 in a manner as shown in FIG. 1, the sterilization apparatus 100 according to this embodiment can deliver the germicidal light in all directions with respect to the main frame 110. That is, the sterilization apparatus 100 according to this embodiment can increase the area illuminated by the germicidal light, as compared with conventional sterilization apparatuses.

Although each of the first sterilization unit 120 and the second sterilization unit 130 is described as including the connection member 160 in this embodiment, it will be understood that the present disclosure is not limited thereto and the connection member 160 may be omitted.

The sterilization apparatus 100 according to this embodiment may include a moving member 140.

The moving member 140 is disposed on an underside of the main frame 110 and helps to move the sterilization apparatus 100.

For example, the moving member 140 may include a wheel. Although the present disclosure is described with reference to an example in which the moving member 140 includes a wheel, it will be understood that the present disclosure is not limited thereto and the moving member 140 may be anything that can help to move the sterilization apparatus 100.

With the moving member 140, the sterilization apparatus 100 according to this embodiment can be easily moved from space to space. Since the sterilization apparatus 100 according to this embodiment can be moved to a space in need of sterilization, there is no need to install the sterilization apparatus in each space. Thus, the sterilization apparatus 100 according to this embodiment can provide high cost saving benefits, as compared with conventional built-in sterilization devices.

Referring to FIG. 3, each of the first sterilization unit 120 and the second sterilization unit 130 may be pivotally coupled to the main frame 110.

Next, other embodiments of the present disclosure will be described. Description of the same components as in the above embodiment will be omitted or briefly given. For details of the same components as in the above embodiment, refer to description given for the above embodiment.

Figure 4:
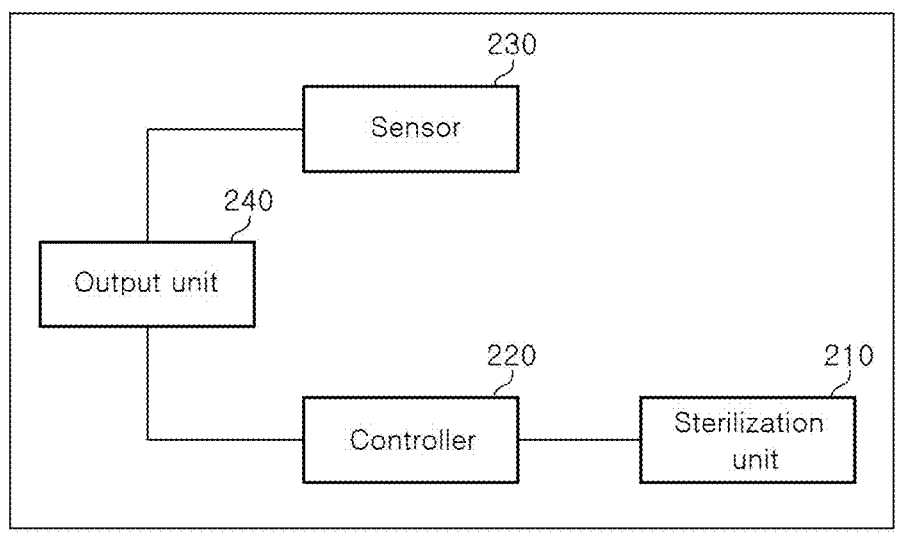
FIG. 4 is a schematic block diagram of a sterilization apparatus according to a second embodiment of the present disclosure.

FIG. 4 is an exemplary view of a sterilization apparatus according to a second embodiment.

Referring to FIG. 4, the sterilization apparatus 200 according to the second embodiment may further include a sensor 230 and a controller 220 besides the components of the sterilization apparatus according to the first embodiment.

The sensor 230 detects a person or an object in a space to be sterilized. That is, with the sensor 230, the sterilization apparatus 200 according to this second embodiment can detect the presence/absence of a person in a space in which sterilization is performed. For example, the sensor 230 may include an ultrasonic sensor, an image sensor, an optical sensor, a pressure sensor, and the like. In addition, the sensor 230 may include any type of sensor that can detect a sterilization target in a space to be sterilized, such as a chemical sensor, a biosensor, and a temperature sensor.

The controller 220 may control operation of the sterilization unit 210 based on signals received from the sensor 230.

The controller 220 may control the sterilization unit 210 to stop emission of the germicidal light in response to a signal from the sensor 230.

For example, when the sensor 230 detects a person in a space to be sterilized, the sensor 230 transmits a signal corresponding thereto to the controller 220. The controller 220 stops sterilization operation of the sterilization unit 210 in response to the signal from the sensor 230.

When there is no person in the space to be sterilized, the sensor 230 transmits a signal corresponding thereto to the controller 220. The controller 220 controls the sterilization unit 210 to resume emission of the germicidal light in response to the signal from the sensor 230.

The sterilization apparatus 200 may further include an output unit 240 displaying detection of an object by the sensor 230.

The output unit 240 may be operated in response to a signal from the sensor 230, or may be operated in response to a signal from the controller 220.

The sterilization apparatus 200 according to this embodiment can prevent a person or an animal from being exposed to the germicidal light through detection of movement of a person or an animal.

Figure 5:
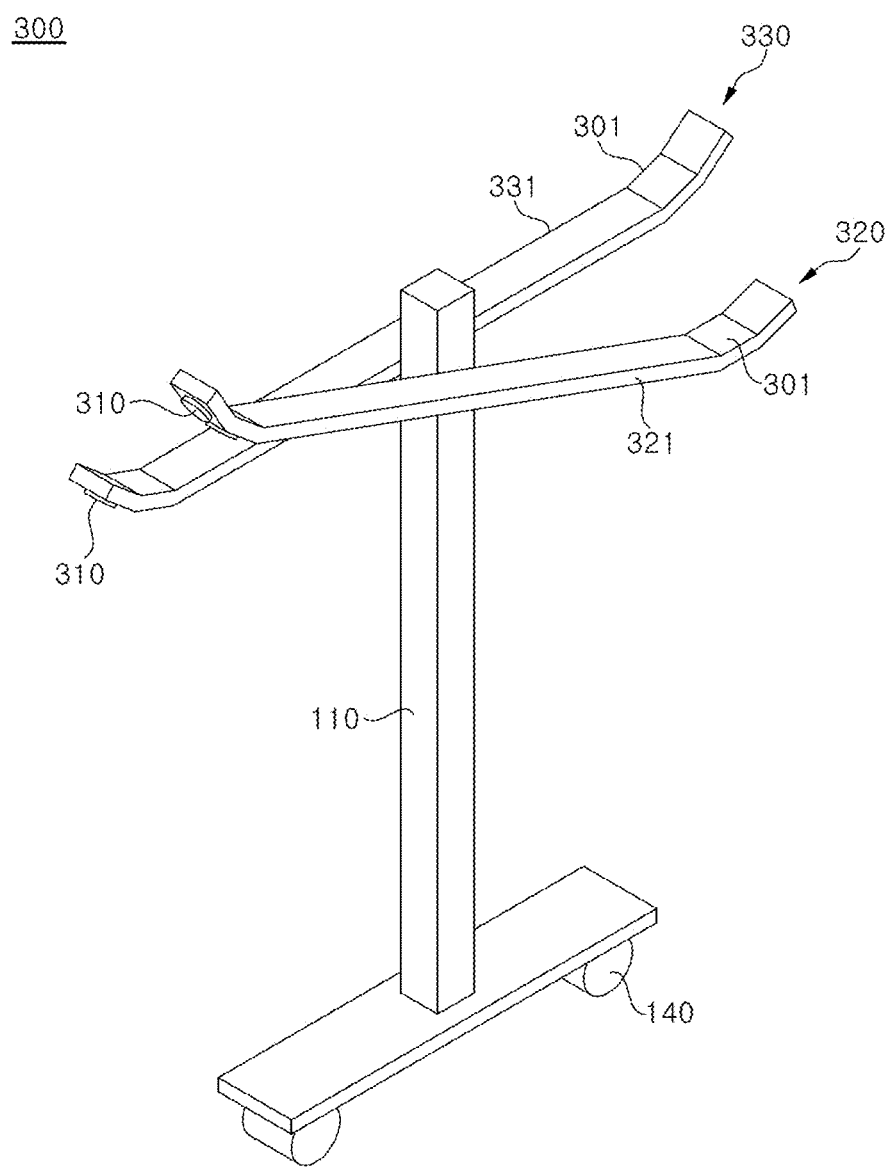
FIG. 5 and FIG. 6 are exemplary views of a sterilization apparatus according to a third embodiment of the present disclosure, where.
Figure 6:
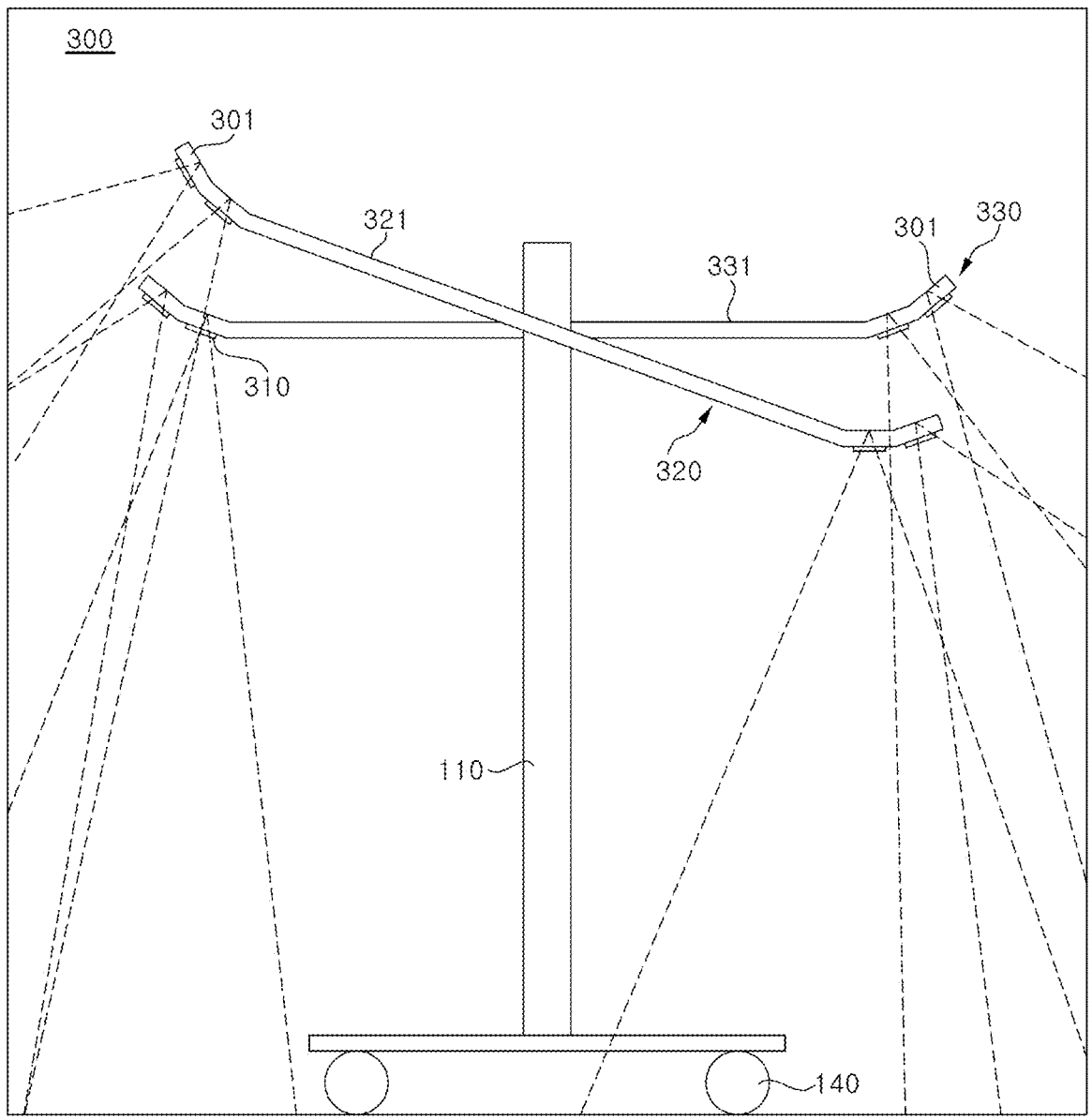

FIG. 5 and FIG. 6 are exemplary views of a sterilization apparatus according to a third embodiment of the present disclosure.

FIG. 5 is a perspective view of the sterilization apparatus 300 according to the third embodiment, and FIG. 6 is a side view of the sterilization apparatus 300 according to the third embodiment.

The sterilization apparatus 300 according to the third embodiment includes a main frame 110, a sterilization unit 320, 330, and a moving member 140.

The main frame 110 extends in the vertical direction and serves to support the sterilization unit.

In this embodiment, the sterilization unit includes a first sterilization unit 320 and a second sterilization unit 330.

Each of the first sterilization unit 320 and the second sterilization unit 330 has a horizontally elongated shape.

The first sterilization unit 320 includes a first support member 321 and multiple germicidal light sources 310 mounted on the first support member 321. The second sterilization unit 330 includes a second support member 331 and multiple germicidal light sources 310 mounted on the second support member 331.

Referring to FIG. 6, the germicidal light source 310 is disposed on a lower surface of each of the first support member 321 and the second support member 331.

Accordingly, the germicidal light source 310 may emit light in a downward direction of the sterilization apparatus 300.

The first support member 321 and the second support member 331 have an elongated shape and are disposed side by side with the main frame 110 interposed therebetween.

In addition, opposite longitudinal ends of each of the first support member 321 and the second support member 331 are movable up and down with a side surface of each of the first support member 321 and the second support member 331 partially secured to a vertical member.

Both longitudinal ends of each of the first support member 321 and the second support member 331 may form multiple mounting portions 301. At least one germicidal light source 310 may be mounted on each of the multiple mounting portions 301.

In addition, the multiple mounting sections 301 may be bendable to various angles.

As shown in FIG. 6, the germicidal light can reach farther depending on bending angles of the mounting portions 301 of the first support member 321 and the second support member 331. In addition, the germicidal light can be delivered laterally as well as downward depending on the bending angles of the mounting sections 301 of the first support member 321 and the second support member 331.

Figure 7:
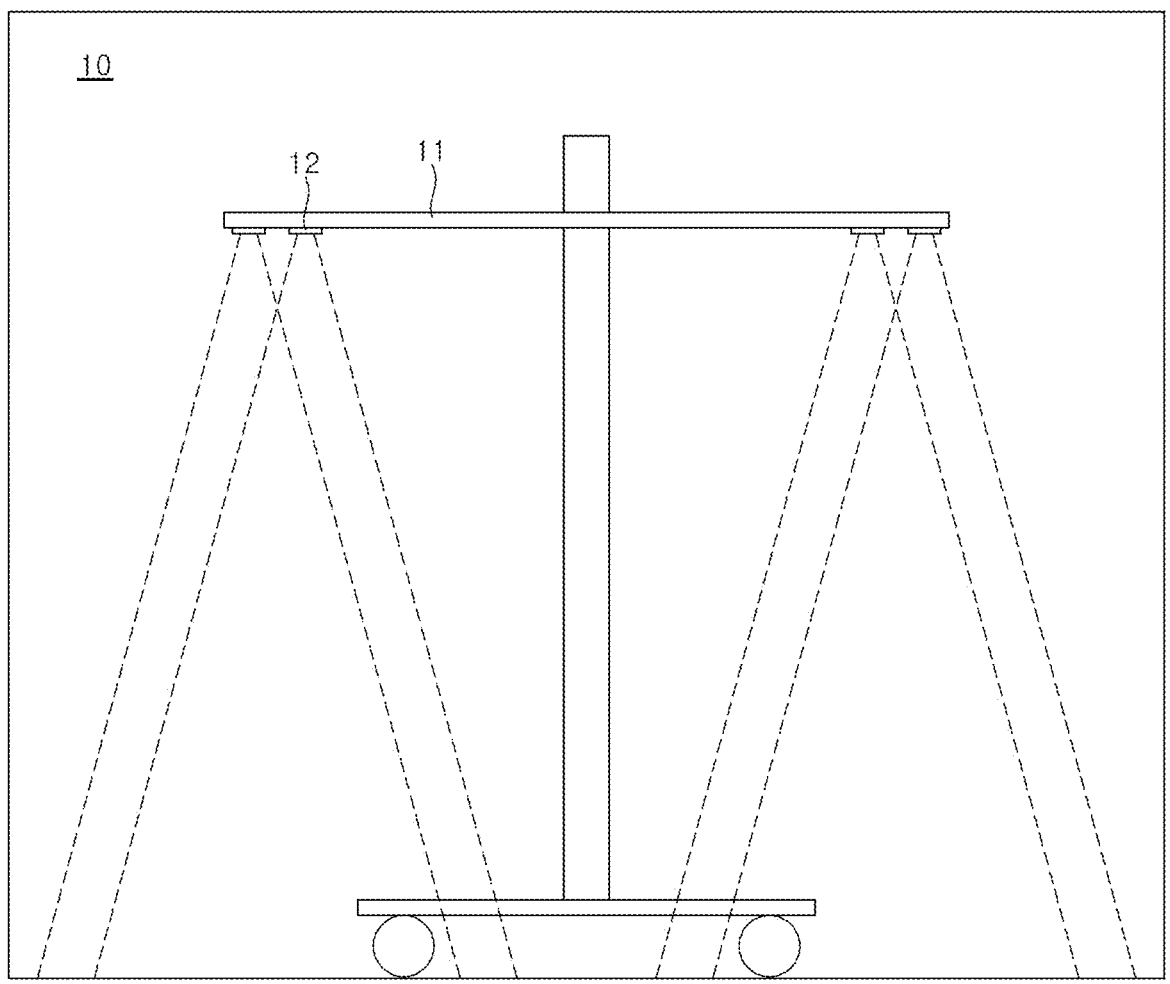
FIG. 7 is a view illustrating illumination range of a sterilization apparatus including a flat support member.

FIG. 7 is an exemplary view illustrating an illumination range of a sterilization apparatus including a flat support member.

In the sterilization apparatus 10 of FIG. 7, due to the flat shape of the support member, all germicidal light sources 12 emit light toward a bottom of a space to be sterilized. That is, the sterilization apparatus 10 can illuminate only a portion of the bottom of the space to be sterilized. Conversely, the sterilization apparatus 300 according to this embodiment can deliver the germicidal light laterally as well as downward with the germicidal light sources 310 disposed only on one surface of each of the first support member 321 and the second support member 331, as shown in FIG. 6.

As can be seen through comparison between FIG. 6 and FIG. 7, in the sterilization apparatus 300, a region illuminated by each germicidal light source can be varied depending on the bending angle of the support member. Thus, the sterilization apparatus 300 can increase sterilization area through adjustment of the bending angle of the support member. In FIG. 6, the germicidal light is shown as not being delivered to some regions of the space to be sterilized. However, the sterilization apparatus 300 according to this embodiment can illuminate the entire region of the space to be sterilized through adjustment of the bending angle of the support member and the number of germicidal light sources.

In addition, when the first support member 321 and the second support member 331 are pivoted to different angles, the germicidal light can be delivered over a larger area.

As such, the sterilization apparatus 300 according to this embodiment can illuminate a large area with the germicidal light using a small number of germicidal light sources through adjustment of the bending angles of the opposite ends of each of the first support member 321 and the second support member 331.

Figure 8:
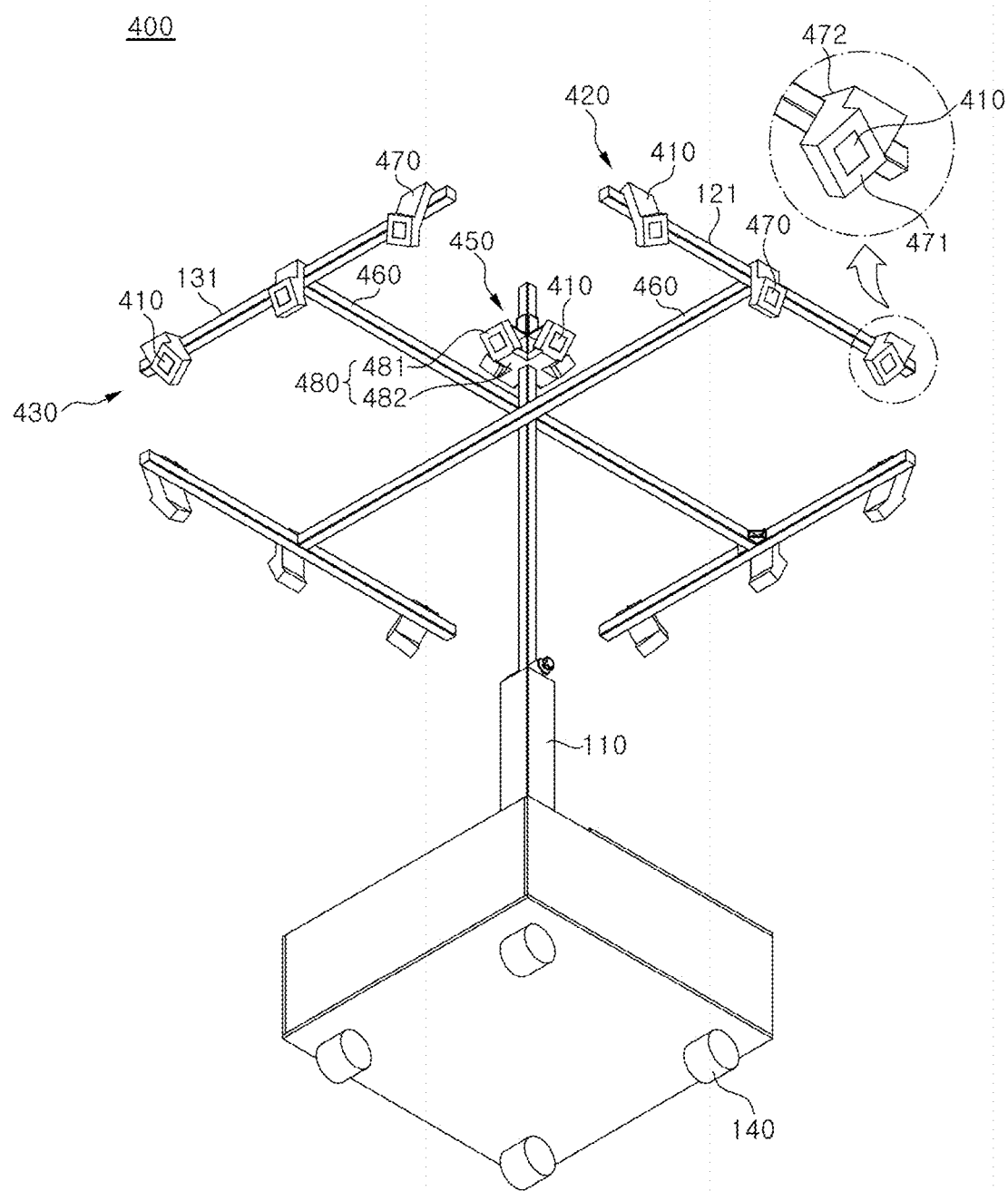
FIG. 8 and FIG. 9 are exemplary views of a sterilization apparatus according to a fourth embodiment of the present disclosure where.
Figure 9:
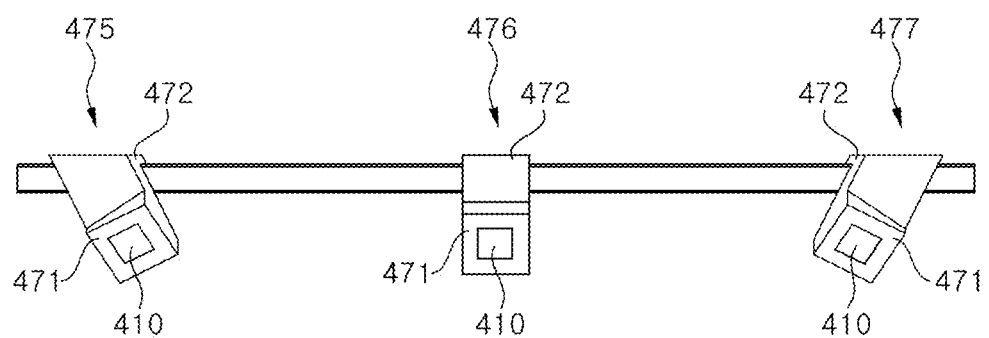

FIG. 8 and FIG. 9 are exemplary views of a sterilization apparatus according to a fourth embodiment of the present disclosure.

Referring to FIG. 8, the sterilization apparatus 400 according to the fourth embodiment includes a main frame 110, a sterilization unit, and a moving member 140. The sterilization unit may be a sterilization module including at least one germicidal light source 410. In this embodiment, the sterilization unit includes a first sterilization units 420, a second sterilization units 430, and a third sterilization unit 450.

The sterilization apparatus 400 according to this embodiment has a structure in which sterilization units are disposed at fours sides of the main frame 110, respectively.

The first sterilization unit 420 includes a first support member 121, a germicidal light source 410, a connection member 460, and a first securing member 470.

The second sterilization unit 420 includes a second support member 131, a germicidal light source 410, a connection member 460, and a first securing member 470.

The connection member 460 of the first sterilization unit 420 is connected at one end thereof to the main frame 110 and is connected at the other end thereof to the first support member 121. The connection member 460 of the second sterilization unit 430 is connected at one end thereof to the main frame 110 and is connected at the other end thereof to the second support member 131.

In this embodiment, the connection member 460 extends from a side surface of the main frame 110.

Thus, the first sterilization unit 420 and the second sterilization unit 430 can deliver the germicidal light farther away from the main frame 110.

Multiple first securing members 470 are mounted on each of the first support member 121 and the second support member 131.

Multiple germicidal light sources 410 are mounted on respective first securing members 470 of each of the first support member 121 and the second support member 131.

The first securing member 470 includes a first mounting surface 471 on which the germicidal light source 410 is mounted and a first securing portion 472 secured to the first support member 121 or the second support member 131.

In this embodiment, the first securing member 470 has a bent shape such that the first securing portion part 472 surrounds the first support member 121 or the second support member 131. However, it will be understood that the present disclosure is not limited thereto and the first securing portion 472 of the first securing member 470 may have any shape that allows the first securing portion 472 to be stably secured to the first support member 121 or the second support member 131.

The first mounting surface 471 is tilted downward at a predetermined angle outwardly of the main frame 110.

In addition, at least one of the multiple first securing members 470 mounted on one support member is tilted in a different direction than the other first securing members 470.

For example, three first securing members 470 may be mounted on each of the first support member 121 and the second support member 131. The three first securing members 470 may be referred to as a $1^{st}$ first securing member 475, a $2^{nd}$ first securing member 476, and a $3^{rd}$ first securing member 477, respectively.

The $2^{nd}$ first securing member 476 and the $3^{rd}$ first securing member 477 are disposed at opposite sides of the $1^{st}$ first securing member 475. Referring to FIG. 9, the first mounting surface 471 of the $2^{nd}$ first securing member 476 and the first mounting surface 471 of the $3^{rd}$ first securing member 477 are tilted at a predetermined angle in opposite directions with respect to the first mounting surface 471 of the $1^{st}$ first securing member 475.

Accordingly, as shown in FIG. 9, the germicidal light sources mounted on the $2^{nd}$ first securing member 476 and the 3rd first securing member 477 can deliver the germicidal light toward a space located outwardly of a corner of the main frame 110.

In the sterilization apparatus 400 according to this embodiment, light exit surfaces of the respective germicidal light sources 410 face in different directions from one another, since the 1st first securing member 475, the 2nd first securing member 476, and the 3rd first securing member 477 face in different directions from one another. Accordingly, the germicidal light sources 410 can deliver the germicidal light in different directions from one another, whereby a larger area can be illuminated with the germicidal light.

In addition, since the light exit surfaces of the respective germicidal light sources 410 face in different directions from one another, the sterilization apparatus 400 according to this embodiment can reduce overlap in illumination between adjacent germicidal light sources 410, as compared with when the light exit surfaces of the respective germicidal light sources 410 face in the same direction. Thus, the sterilization apparatus 400 according to this embodiment can improve uniformity of illumination with the germicidal light, as compared with when the light exit surfaces of the respective germicidal light sources 410 face in the same direction. That is, the sterilization apparatus 400 according to the present embodiment can improve irradiance uniformity across the entire sterilization target through minimization of overlap in illumination between adjacent germicidal light sources 410.

In particular, due to the structures of the 2nd first securing members 476 and the 3rd first securing member 477 disposed at the opposite ends of the support member, the sterilization apparatus 400 can also deliver the germicidal light to corners of a space to be sterilized, which would otherwise be generally unreachable by the germicidal light.

The first securing member 470 may include a component for supplying power to the germicidal light source 410. For example, the first securing member 470 may include a circuit board formed with an interconnect electrically connected to the germicidal light source 410. Alternatively, the first securing member 470 may include a cable connected to the germicidal light source 410.

The third sterilization unit 450 includes a second securing member 480 and a germicidal light source 410 mounted on the second securing member 480.

Referring to FIG. 8, the third sterilization unit 450 is mounted on each side surface of the main frame 110. However, it will be understood that the third sterilization unit 450 is not necessarily mounted on the main frame 110. The third sterilization unit 450 may be mounted on the connection member 460. In addition, although the third sterilization unit 450 is shown as being disposed above the connection member 460, it will be understood that the present disclosure is not limited thereto and the third sterilization unit 450 may be disposed below the connection member 460. Further, the third sterilization unit 460 may be disposed between the connection members 460 to deliver the germicidal light through a space between the first sterilization unit 420 and the second sterilization unit 430.

The second securing member 480 includes a second mounting surface 481 on which the germicidal light source 410 is mounted and a second securing portion 482 secured to the main frame 110.

The second securing member 480 is coupled at one end thereof to a side surface of the main frame 110. Here, the one end of the second securing member 480 corresponds to the second securing portion 482. In FIG. 8, the second fixing portion 482 is simply shown as adjoining the side surface of the main frame 110. However, it will be understood that the present disclosure is not limited thereto and the second securing portion 482 may have any structure that allows the second securing portion 482 to be secured to the main frame 110.

In addition, a portion of the other end of the second securing member 480 is tilted upward at a predetermined angle with respect to a body of the second securing member 480. Here, a lower surface of the inclined portion corresponds to the second mounting surface 481.

Thus, the second mounting surface 481 faces sideways with respect to the main frame 110 and is tilted downward at a predetermined angle.

Accordingly, the germicidal light source 410 mounted on the second mounting surface 481 emits the germicidal light diagonally toward a region under the sterilization unit. In this way, the germicidal light source 410 can deliver the germicidal light over a larger area.

Like the first securing member 470, the second securing member 480 may include a component for supplying power to the germicidal light source 410.

With the first sterilization unit 420 and the second sterilization unit 430 outwardly spaced a predetermined distance apart from the main frame 110, the sterilization apparatus 400 according to this embodiment can deliver the germicidal light to regions far away from the main frame 110. In addition, with the third sterilization unit 450, the sterilization apparatus 400 can deliver the germicidal light to a region between the main frame 110 and the first sterilization unit 420 or the second sterilization unit 430.

Accordingly, with the first sterilization unit 420, the second sterilization unit 430, and the third sterilization unit 450, the sterilization apparatus 400 according to this embodiment can uniformly deliver the germicidal light over a large area.

Table 1 shows the position and angle of each germicidal light source 410 according to this embodiment.

TABLE 1

| | Position of germicidal light source (m) | | | Angle of germicidal light source (deg.) | | |
|---|---|---|---|---|---|---|
| | X | Y | Z (height) | α | β | γ |
| Germicidal light source on 1st first securing member | 0.8 | 0.0 | 2.0 | — | −65 | — |
| Germicidal light source on second securing member | 0.1 | 0.0 | 2.0 | — | −50 | — |
| Germicidal light source on 2nd first securing member | 0.8 | 0.4 | 1.9 | — | −60 | −55 |
| Germicidal light source on 3rd first securing member | 0.8 | −0.4 | 2.0 | — | −60 | 55 |

The germicidal light sources 410 shown in Table 1 are germicidal light sources 410 disposed at one side of the main frame 110. In the sterilization apparatus 400 according to this embodiment, a set of germicidal light sources 410 as shown in Table 1 is disposed at each of the four sides of the main frame 110.

Assuming each germicidal light source 410 includes one light emitting diode, a total of 16 light emitting diodes is used in the sterilization apparatus 400 according to this embodiment.

The present disclosure has been described with reference to an example in which the sterilization units of the sterilization apparatus 400 according to this embodiment are connected to the main frame 110 through respective connection members 460. However, it will be understood that the present disclosure is not limited thereto and the sterilization apparatus 300 according to this embodiment may have a different structure.

By way of another example, the first sterilization unit 420 and the second sterilization unit 430 may be connected to a common connection member 460.

For example, the sterilization apparatus 400 may include two connection members 460 connected to the main frame 110. Each of the connection members 460 may be connected at one end thereof to the first sterilization unit 420 and the second sterilization unit 430 and may be connected at the other end thereof to the main frame 110.

One end of the support member 121 of the first sterilization unit 420 and one end of the support member 131 of the second sterilization unit 430 may be connected to the one end of the connection member 460. Here, the first sterilization unit 420 and the second sterilization unit 430 may be disposed to face in opposite directions and to be symmetrical with respect to the one end of the connection member 460.

In addition, with the one end of each of the first sterilization unit 420 and the second sterilization unit 430 connected to the one end of the connection member 460, the other end of each of the first sterilization unit 420 and the second sterilization unit 430 may be moved outwardly or inwardly of the connection member 430. That is, in the sterilization apparatus 400, the sterilization unit may be folded or unfolded with respect to the connection member 460.

The two connection members 460 may also be folded or unfolded with respect to the main frame 110. In addition, the main frame 110 is adjustable in length. Further, these motions of the sterilization apparatus 400 may be automatically performed to improve user convenience.

Accordingly, the sterilization apparatus 400 can be carried or stored in compact form with the sterilization units and the connection member 460 folded and the main frame minimized in length.

FIG. 10 shows comparison in light distribution between a conventional sterilization apparatus and the sterilization apparatus according to this embodiment.

Figures 10A, 10B, 10C:
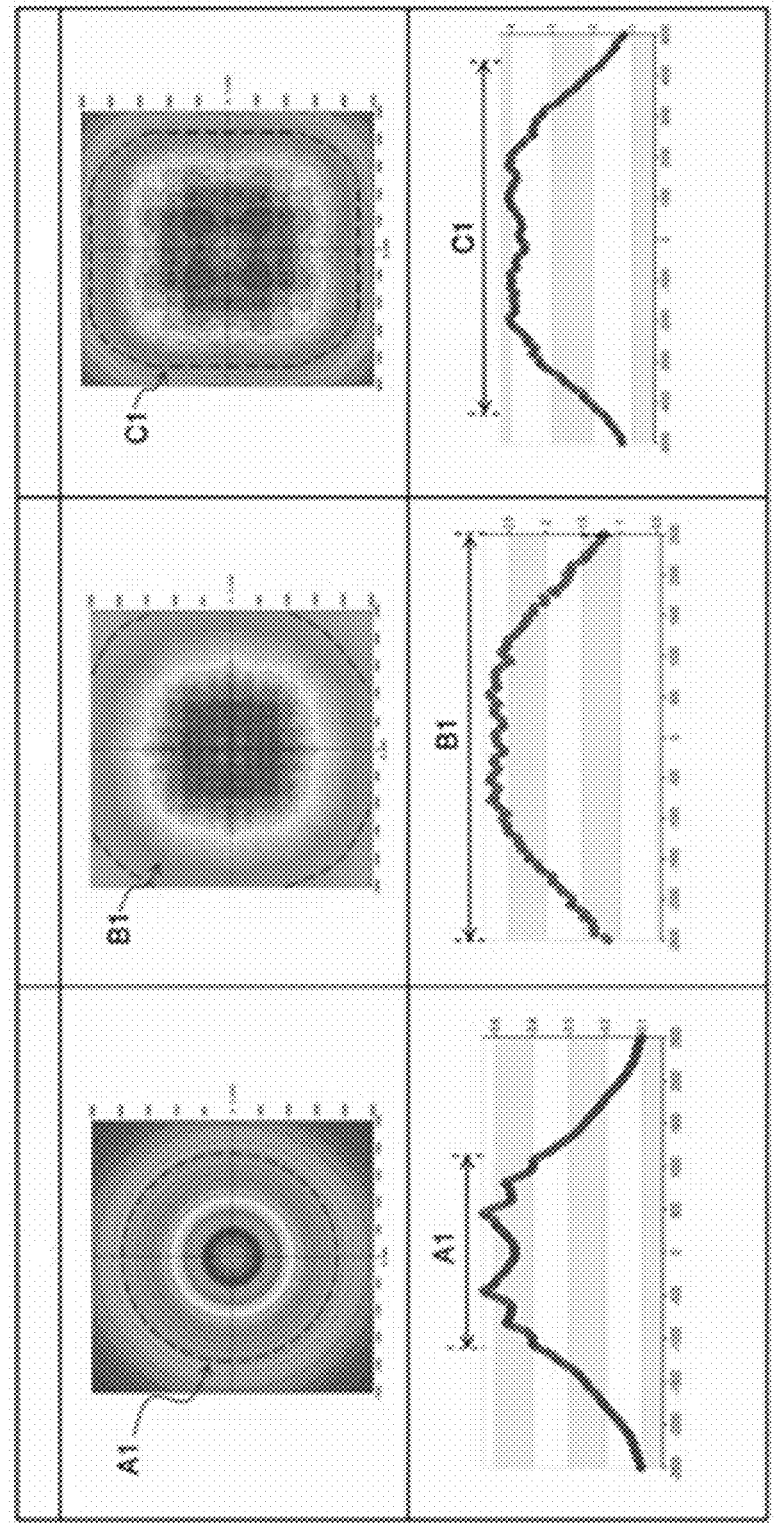
FIG. 10A through FIG. 10C show comparison in light distribution between a conventional sterilization apparatus and the sterilization apparatus according to the fourth embodiment, where.

FIG. 10A shows a light distribution produced by the conventional sterilization apparatus and FIG. 10B shows a light distribution produced by the sterilization apparatus according to this embodiment. FIG. 10C shows a light distribution produced by four sterilization apparatuses according to this embodiment disposed around the center of a space to be sterilized. Here, "light distribution" refers to a distribution of the germicidal light delivered to the space to be sterilized by each of the sterilization apparatuses. In addition, the graphs of FIGS. 10A through 10C show irradiance levels of the germicidal light, as measured along the X-axis from the center of the space to be sterilized.

The conventional sterilization apparatus (FIG. 10A) includes a sterilization unit located 2 m above the floor, wherein light exit surfaces of respective germicidal light sources of the sterilization unit face in the same direction.

The sterilization apparatus according to this embodiment (FIG. 10B) includes a sterilization unit including germicidal light sources disposed as shown in FIG. 8 and Table 1. That is, in the sterilization apparatus of FIG. 10B, respective light exit surfaces of the germicidal light sources face in different directions from one another such that the germicidal light sources emit the germicidal light in different directions from one another.

In FIG. 10C, four sterilization apparatuses, identical to the sterilization apparatus of FIG. 8, are disposed in the space to be sterilized. Here, the four sterilization apparatus are disposed in four sections around the center of the space to be sterilized, respectively. Here, one sterilization apparatus is spaced 4 m apart from adjacent sterilization apparatuses. Here, the sterilization units of the sterilization apparatuses of FIG. 10B and FIG. 10C are also located 2 m above the floor.

FIG. 10A and FIG. 10B show simulation results for a space having an area of 25 m² (5 m×5 m (width×length)), and FIG. 10C shows simulation results for a space having an area of 100 m² (10 m×10 m (width×length)).

Here, the sterilization apparatus according to this embodiment, used in the simulations, has a length of about 1.6 m, wherein the length is a distance between opposite horizontal ends thereof. In addition, the simulation results are irradiances measured at the bottom of the space to be sterilized.

In FIG. 10A, FIG. 10B, and FIG. 10C, the regions marked in red and green (A1, B1, C1) are regions illuminated with a sufficient amount of the germicidal light for sterilization. That is, A1, B1, and C1 are regions than can be sterilized to a sufficient degree. In FIG. 10A, FIG. 10B, and FIG. 10C, the regions marked in blue are regions illuminated with an insufficient amount of the germicidal light for sterilization. In FIGS. 10A, 10B and 10C, the blue regions are located outside A1, B1, and C1.

Referring to FIG. 10A, in the conventional sterilization apparatus, intensity of the germicidal light is high only in a central region of the space to be sterilized and decreases sharply as distance from the central region increases. That is, the graph of FIG. 10A shows that the conventional sterilization apparatus exhibits poor overall illumination uniformity. In this case, most regions, except for the central region close to the germicidal light sources, cannot be properly sterilized. In particular, corner regions are supplied with little or no germicidal light.

Referring to FIG. 10B and FIG. 10C, it can be seen that the sterilization apparatus according to this embodiment can deliver a sufficient amount of germicidal light for sterilization over a large area, as compared with the conventional sterilization apparatus. In addition, it can be seen that the sterilization apparatus according to this embodiment provides uniform light distribution, as compared with the conventional sterilization apparatus.

Referring to FIG. 10B, in the sterilization apparatus according to this embodiment, a deviation in irradiance across regions of the space to be sterilized is less than 50% of a maximum irradiance. That is, a difference between an average irradiance across the regions of the space to be sterilized and a maximum irradiance is less than 50% of the maximum irradiance. Accordingly, it can be seen that the sterilization apparatus according to this embodiment can ensure uniform irradiance across the regions of the space to be sterilized.

In addition, the sterilization apparatus according to this embodiment achieves a uniformity of illumination of 75% or more across the regions of the space to be sterilized. That is, it can be seen that the sterilization apparatus according to this embodiment can ensure uniform illumination over a large area, as compared with the conventional sterilization apparatus.

Further, it can be seen that the sterilization apparatus according to this embodiment can illuminate corner regions with the germicidal light at high intensity, as compared with the conventional sterilization apparatus.

That is, the results in FIGS. 10A, 10B and 10C show that the sterilization apparatus according to this embodiment can uniformly illuminate a large area with the germicidal light at a high intensity, as compared with the conventional sterilization apparatus. In addition, the sterilization apparatus according to this embodiment can deliver the germicidal light throughout the space to be sterilized, including corner regions, which are supplied with little or no germicidal light by the conventional sterilization apparatus.

Figure 11:
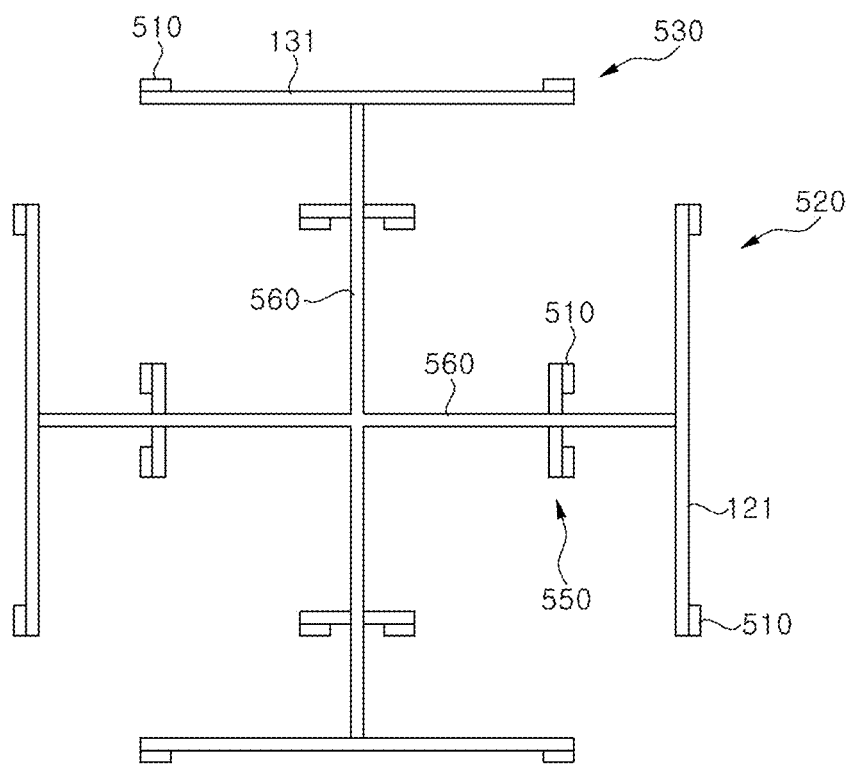
FIG. 11 is a schematic plan view of a sterilization apparatus according to a fifth embodiment of the present disclosure.

FIG. 11 is a schematic plan view of a sterilization apparatus according to a fifth embodiment of the present disclosure.

Referring to FIG. 11, the sterilization apparatus 500 according to the fifth embodiment includes a pair of first sterilization units 520, a pair of second sterilization units 530, and multiple third sterilization units 550.

Although not shown in FIG. 11, the sterilization apparatus 500 may further include a main frame and a moving member.

The first sterilization unit 520, the second sterilization unit 530, and the third sterilization unit 550 may have substantially the same structure as the sterilization units according to the above embodiments. In this embodiment, description will be made mainly on differences from the above embodiments in terms of arrangement of germicidal light sources 510 of each sterilization unit.

Referring to FIG. 11, the first sterilization unit 520 has a structure in which two germicidal light sources 510 are mounted at opposite ends of a first support member 121, respectively. In addition, the second sterilization unit 530 has a structure in which two germicidal light sources 510 are mounted at opposite ends of the second support member 131, respectively.

Although each of the first sterilization unit 520 and the second sterilization unit 530 is shown as including only the two germicidal light sources 510 mounted at the opposite ends of the support member, it will be understood that the present disclosure is not limited thereto and each of the first sterilization unit 520 and the second sterilization unit 530 may further include a germicidal light source 510 mounted at the center of the support member, as shown in FIG. 8.

The multiple third sterilization units 550 are mounted on respective connection members 560. Like the first sterilization unit 520 and the second sterilization unit 530, the third sterilization unit 550 has a structure in which two germicidal light sources 510 are mounted at opposite ends of a horizontally elongated support member, respectively. Alternatively, the third sterilization unit 550 may have the same structure as the third sterilization unit of FIG. 8 except that the third sterilization unit 550 is mounted on the connection member 560.

The third sterilization unit 550 may be disposed midway between the main frame 110 and the support member to emit the germicidal light to a space between the main frame 110 and the support member.

In addition, the germicidal light sources 510 of the third sterilization unit 550 may be disposed between the two germicidal light sources 510 of the first sterilization unit 520 or the second sterilization unit 530. In this way, the third sterilization unit 550 can deliver the germicidal light to a region corresponding to the center of the first sterilization unit 520 or the second sterilization unit 530, which would otherwise be likely to be supplied with a relatively insufficient amount of light, as compared with regions corresponding to the opposite ends of the first sterilization unit 520 or the second sterilization unit 530.

The third sterilization unit 550 is mounted on the connection member 560 to be movable along the connection member 560. That is, the third sterilization unit 550 can be moved between the main frame 110 and the support member along the connection member 560 to deliver the germicidal light to a region in short supply of the germicidal light.

The germicidal light sources 510 of each of the first sterilization unit 520, the second sterilization unit 530, and the third sterilization unit 550 may be mounted on the support member to face sideways or downwards. Alternatively, the germicidal light sources 510 may be mounted on the support member to face in different directions.

In addition, each of the first sterilization unit 520, the second sterilization unit 530, and the third sterilization unit 550 may be adjustable in angle with respect to the vertical direction. Here, each of the sterilization units may be individually adjustable in angle with respect to the vertical direction.

In this way, the sterilization apparatus 500 according to this embodiment can uniformly deliver the germicidal light throughout a space to be sterilized through adjustment of the angles of the first sterilization unit 520, the second sterilization unit 530, and the third sterilization unit 550 or movement of the third sterilization unit 550.

Figure 12:
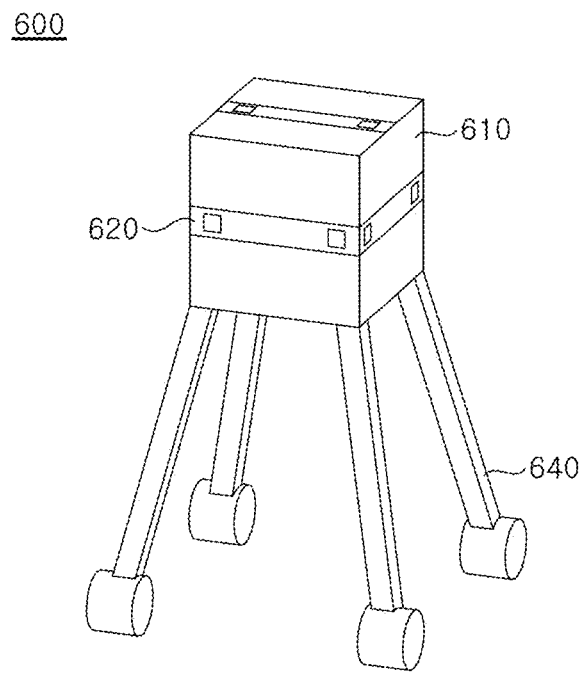
FIG. 12 and FIG. 13 are exemplary views of a sterilization apparatus according to a sixth embodiment of the present disclosure where.
Figure 13:
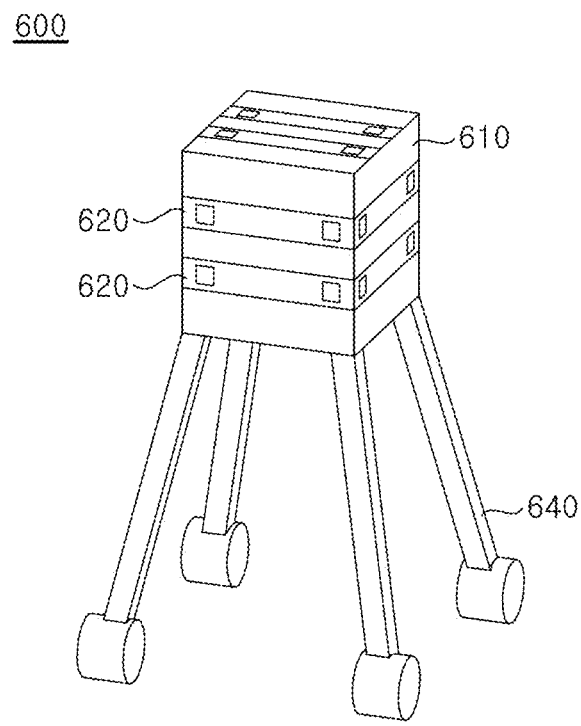

FIG. 12 and FIG. 13 are exemplary views of a sterilization apparatus according to a sixth embodiment of the present disclosure.

The sterilization apparatus 600 according to the sixth embodiment includes a main frame 610, a sterilization unit 620, and a moving member 640.

Referring to FIG. 12, the main frame 610 has a cuboidal shape. In addition, the sterilization unit 620 includes multiple sterilization units disposed on the upper surface and four side surfaces of the main frame 610, respectively.

The moving member 640 includes a wheel to facilitate movement of the sterilization apparatus 600. In addition, the moving member 640 has an elongated shape and supports the main frame 610 with a space between the main frame 610 and the floor.

In this way, the sterilization unit 620 mounted on the main frame 610 can be located at an upper portion of a space to be sterilized rather than at a bottom of the space and thus can deliver the germicidal light over a large area.

Although not shown, the sterilization apparatus 600 according to this embodiment may further include a sterilization unit 620 mounted on a lower surface of the main frame 610.

Due to the elongated shape of the moving member 640, there can be a large region unreachable by the germicidal light under the main frame 610.

The sterilization unit 620 mounted on the lower surface of the main frame 610 can deliver the germicidal light to the region under the main frame 610.

The sterilization apparatus 600 according to this embodiment allows adjustment of the number of sterilization units 620 as necessary.

Since the main frame 610 of the sterilization apparatus 600 according to this embodiment has a cuboidal shape, rather than an elongated rod-like shape as in the above embodiments, the main frame 610 can secure a large surface area for mounting the sterilization unit 620.

Accordingly, as shown in FIG. 13, an additional sterilization unit 620 may be disposed on each surface of the main frame 610, as needed.

Although the same number of sterilization units 620 is disposed on each surface of the main frame 610 in FIG. 12 and FIG. 13, it will be understood that the present disclosure is not limited thereto and a different number of sterilization units 620 may be disposed on each surface of the main frame 610, as needed.

Figure 14:
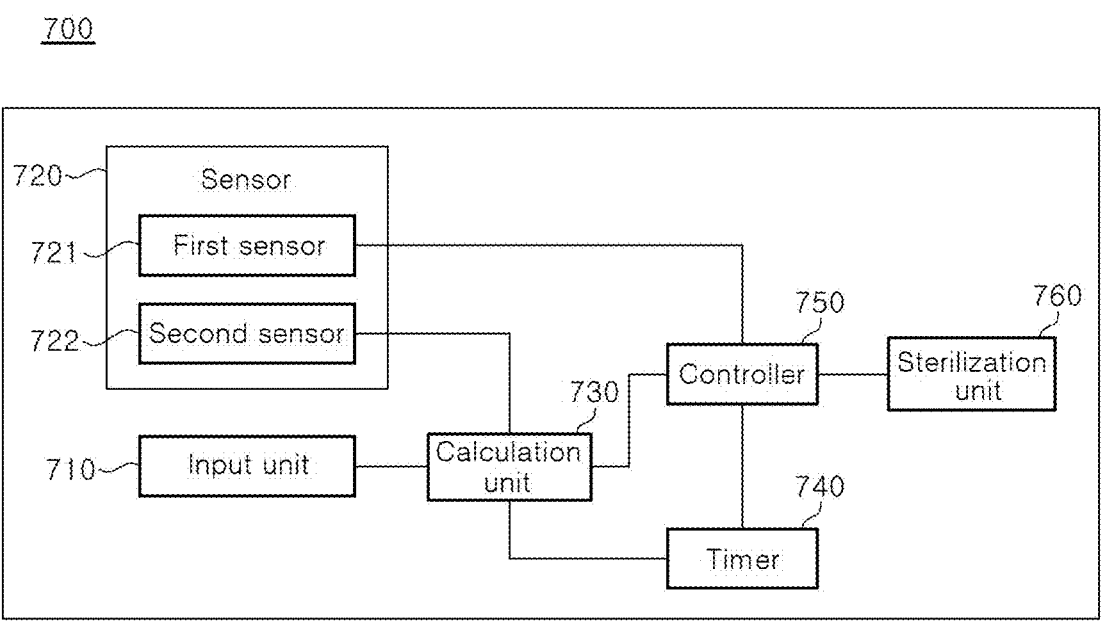
FIG. 14 is a schematic block diagram of a sterilization apparatus according to a seventh embodiment of the present disclosure.

FIG. 14 is a schematic block diagram of a sterilization apparatus according to a seventh embodiment of the present disclosure.

The sterilization apparatus 700 according to the seventh embodiment may further include an input unit 710, a sensor 720, a calculation unit 730, a timer 740, and a controller 750, besides the components of each of the sterilization apparatuses according to the above embodiments. Here, the input unit 710 and the sensor 720 may be disposed outside a body of the sterilization apparatus 700. In addition, the calculation unit 730, the timer 740, and the controller 750 may be disposed inside the body of the sterilization apparatus 700.

The sterilization apparatus 700 according to the seventh embodiment may have the same external shape as any of the sterilization apparatuses according to the first to sixth embodiments. For details of a main frame, a moving member, and a sterilization unit 760 of the sterilization apparatus 700 according to the seventh embodiment, description given for the sterilization apparatuses according to the above embodiments can be used.

The input unit 710 is adapted to input signals therethrough.

The sensor 720 detects an object in a space to be sterilized and measures a distance to the object.

The calculation unit 730 calculates conditions under which the sterilization apparatus 700 performs sterilization, such as sterilization time and intensity of the germicidal light, in response to signals from the input unit 710 and the sensor 720.

The timer 740 receives information about sterilization time from the input unit 710 or the calculation unit 730 and transmits a signal corresponding to the information to the controller 750.

The controller 750 controls operation of the sterilization unit 760 based on signals from at least one of the sensor 720, the calculation unit 730, and the timer 740.

Now, each component of the sterilization apparatus 700 according to this embodiment will be described in more detail.

The sterilization apparatus 700 may receive an external setting signal via the input unit 710. For example, the setting signal may be a sterilization time signal containing information about sterilization time.

That is, a user may input sterilization time to the sterilization apparatus 700 via the input unit 710. For example, the input unit 710 may include any input device that can be used to input information, such as a button or a touchpad. The input unit 710 may transmit the sterilization time signal containing information about the input sterilization time to the calculation unit 730. In addition, the input unit 710 may transmit the sterilization time signal to both the calculation unit 730 and the timer 740.

The sensor 720 may include at least one sensor. In this embodiment, the sensor 720 may include a first sensor 721 and a second sensor 722.

The first sensor 721 may be a sensor that detects an object within a predetermined range of distances from the sterilization apparatus 700. For example, the first sensor 721 may be an object detection sensor.

The first sensor 721 may generate a first sterilization termination signal upon detecting movement of an object in a space to be sterilized. Here, the movement of the object may be movement of a person or an animal. The first sensor 721 may transmit the generated first sterilization termination signal to the controller 750.

In addition, the first sensor 721 may transmit a first sterilization start signal to the controller 750 upon detecting that the detected object has left the space to be sterilized.

The controller 750 may shut off power supply to the sterilization unit 760 in response to the first sterilization termination signal from the first sensor 721.

In addition, the controller 750 may initiate power supply to the sterilization unit 760 in response to the first sterilization start signal from the first sensor 721.

As such, the sterilization apparatus 700 according to this embodiment can stop sterilization when a person or an animal enters a space where sterilization is in progress. Accordingly, the sterilization apparatus 700 can prevent a person or an animal from being exposed to the germicidal light.

The second sensor 722 may include a distance sensor that measures a distance to a sterilization target. For example, when the sterilization target is a space, the distance sensor may measure distances to walls defining the space. That is, the second sensor 722 may measure the size of a space to be sterilized.

The second sensor 722 may generate a sterilization distance signal containing information about the measured distance to the sterilization target. In addition, the second signal may transmit the generated sterilization distance signal to the calculation unit 730.

The calculation unit 730 may receive the sterilization time signal from the input unit 710 and may receive the sterilization distance signal from the second sensor 722.

The calculation unit 730 may calculate information necessary for sterilization based on the information about the sterilization time and the information about the distance to the sterilization target, which are contained in the respective received signals.

Figure 15:
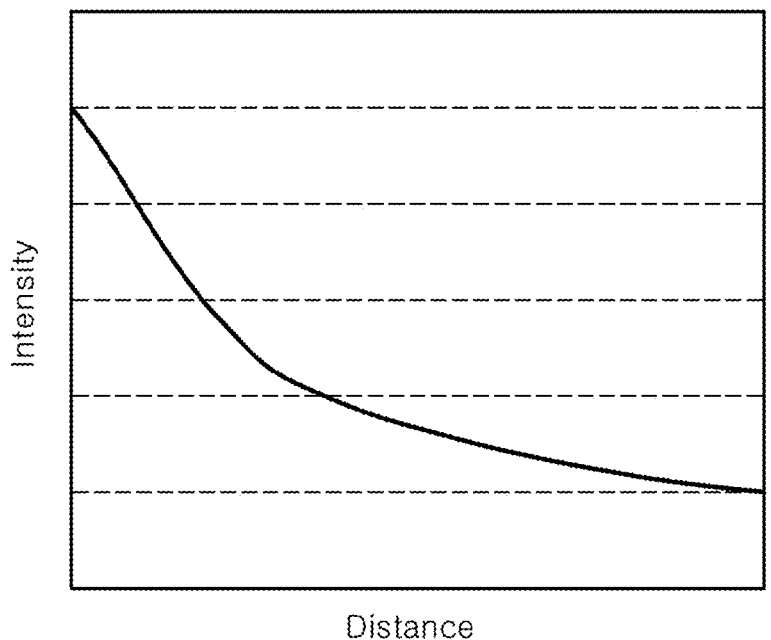
FIG. 15 is a graph showing changes in intensity depending on travel distance of germicidal light.
Figure 16:
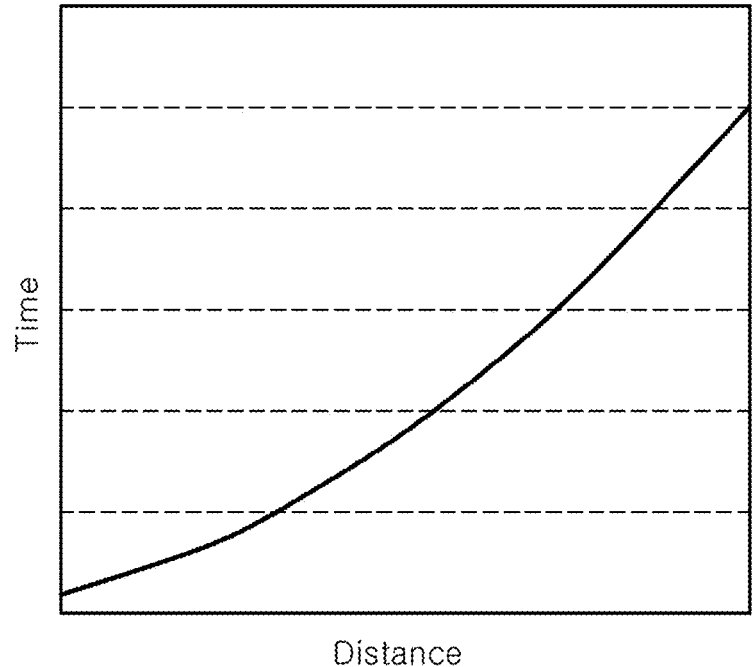
FIG. 16 is a graph showing changes in sterilization time depending on travel distance of germicidal light.
Figure 17:
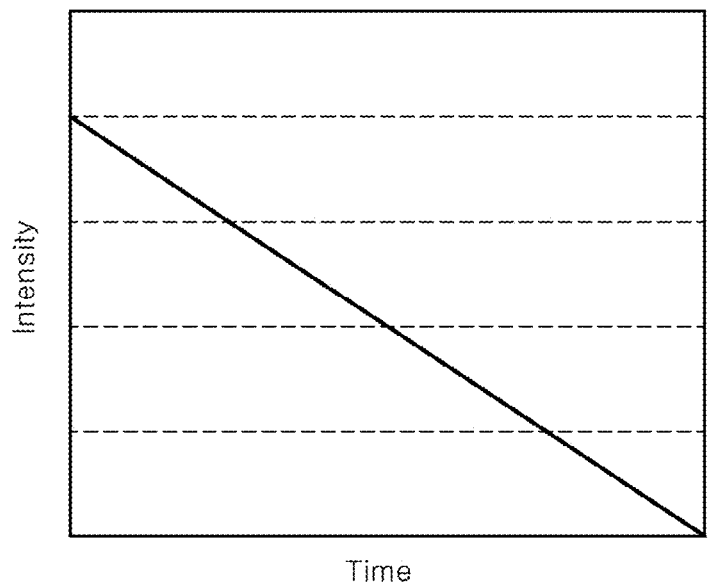
FIG. 17 is a graph showing changes in sterilization time depending on intensity of germicidal light.

FIG. 15 is a graph showing changes in intensity depending on travel distance of the germicidal light. FIG. 16 is a graph showing changes in sterilization time depending on travel distance of the germicidal light. FIG. 17 is a graph showing changes in sterilization time depending on intensity of the germicidal light.

Results in FIG. 15 show that intensity of the germicidal light delivered to a sterilization target is inversely proportional to the square of a travel distance of the germicidal light.

Results in FIG. 16 show that required sterilization time increases with increasing travel distance of the germicidal light.

Results in FIG. 17 show that intensity of the germicidal light incident on a surface of the sterilization target is inversely proportional to sterilization time.

Controlled conditions for sterilization of the sterilization target may be represented by Equations 1 to 5:

$$I = \alpha \times P0 \times 1/r^2 \quad \text{[Equation 1]}$$

From Equation 1, it is possible to obtain the travel distance-dependent light power of germicidal light sources required for sterilization.

$$D = I \times T = \alpha \times P0 \times 1/r^2 \times T \quad \text{[Equation 2]}$$

From Equation 2, it is possible to know relations between intensity of the germicidal light required for sterilization and travel distance of the germicidal light or sterilization time.

$$T = D \times r^2 \times 1/\alpha \times 1/P0 \quad \text{[Equation 3]}$$

From Equation 3, it is possible to obtain the amount of sterilization time depending on travel distance of the germicidal light and intensity of the germicidal light required for sterilization.

$$P0 = D \times r^2 \times 1/\alpha \times 1/T \quad \text{[Equation 4]}$$

From Equation 4, it is possible to know relations between travel distance of the germicidal light, sterilization time, intensity of the germicidal light required for sterilization, and light power of the germicidal light sources.

$$r^2 = P_0 \times \alpha \times T \times 1/D = \alpha \cdot P_0 \cdot T/D \quad \text{[Equation 5]}$$

From Equation 4, it is possible to know relations between light power of the germicidal light sources, sterilization time, intensity of the germicidal light required for sterilization, and travel distance of the germicidal light.

In Equations 1 to 5, I is an intensity (unit: $mW/cm^2$) of the germicidal light incident per unit surface area of the sterilization target, $P_0$ is a light power (unit: mW) of the germicidal light sources, T is an amount (unit: sec) of sterilization time, D is a dose (unit: $mJ/cm^2$) of the germicidal light delivered per unit surface area of the sterilization target, r is a distance (unit: cm) to the sterilization target (travel distance), and a is an experimental constant. Here, the experimental constant is a value determined through experiments on relations between the light power ($P_0$) of the germicidal light sources and the intensity (I) of the germicidal light incident on the surface of the sterilization target.

The calculation unit 730 may calculate various types of information necessary for sterilization based on information calculated according to Equations 1 to 5.

In this embodiment, the calculation unit 730 may calculate an intensity of the germicidal light required to sufficiently sterilize a space to be sterilized based on the information about the distance to the sterilization target, which is received from the second sensor 722.

The calculation unit 730 may transmit a sterilization intensity signal containing information about the calculated intensity of the germicidal light to the controller 750.

In addition, the calculation unit 730 may transmit the sterilization time signal received from the input unit 710 to the timer 740.

The timer 740 may receive the sterilization time signal from the input unit 710 or the calculation unit 730.

In addition, the timer 740 may transmit a second sterilization start signal and a second sterilization termination signal to the controller 750 based on the received sterilization time signal.

The controller 750 may receive the sterilization intensity signal from the calculation unit 730 and may receive the second sterilization start signal and the second sterilization termination signal from the timer 740.

The controller 750 may control the amount of current supplied to the sterilization unit 760 based on the sterilization intensity signal received from the calculation unit 730. That is, the controller 750 may control the intensity of the germicidal light emitted from the sterilization unit 760 through control over the amount of current supplied to the sterilization unit 760.

In addition, the controller 750 may initiate power supply to the sterilization unit 760 in response to the second sterilization start signal from the timer 740. Further, the controller 750 may shut off power supply to the sterilization unit 760 in response to the second sterilization termination signal from the timer 740.

In this way, the sterilization apparatus 700 according to this embodiment can automatically adjust the intensity of the germicidal light based on the measured distance to the sterilization target to complete sterilization in the input sterilization time.

Although the present disclosure has been described with reference to an example in which sterilization time is set via the input unit 710, it will be understood that settings input via the input unit 710 is not limited thereto.

In another embodiment, intensity of the germicidal light may be set via the input unit 710. In this embodiment, the calculation unit 730 may calculate sterilization time based on the intensity of the germicidal light set via the input unit 710.

The calculation unit 730 may transmit a sterilization time signal containing information about the calculated sterilization time to the timer 740.

The timer 740 may transmit the second sterilization start signal and the second sterilization termination signal to the controller 750 based on the sterilization time signal received from the calculation unit 730.

The controller 750 may initiate or shut off power supply to the sterilization unit 760 in response to the second sterilization start signal or the second sterilization termination signal received from the timer 740. That is, the controller 750 may control the time the sterilization unit 760 starts or stops operation in response to the second sterilization start signal or the second sterilization termination signal.

In addition, the controller 750 may receive information about the intensity of the germicidal light from the input unit 710 or the calculation unit 730. Accordingly, the controller 750 may control operation of the sterilization unit 760 in response to the signals from the timer 740 while controlling the intensity of the germicidal light through control over the amount of current supplied to the sterilization unit 760.

In a further embodiment, the sterilization apparatus 700 may automatically calculate sterilization time and may perform sterilization for the calculated sterilization time.

The calculation unit 730 may calculate sterilization time based on the information about the distance to the sterilization target, which is received from the second sensor 722.

That is, without user input of sterilization time via the input unit 710, the calculation unit 730 can calculate sterilization time required for sterilization based on the distance to the sterilization target and the preset basic intensity of the germicidal light. The calculation unit 730 may generate a sterilization time signal and may transmit the generated sterilization time signal to the timer 740.

In this way, the sterilization apparatus 700 according to this embodiment of the present disclosure can perform efficient sterilization through automatic calculation of sterilization time, sterilization intensity, sterilization range, and the like, based on input information.

Although the present disclosure has been described with reference to some embodiments in conjunction with the accompanying drawings, it should be understood that these embodiments are provided for illustration only and are not to be construed in any way as limiting the present disclosure. The scope of the present disclosure should be defined by the appended claims and equivalents thereto.

The invention claimed is:
1. A light emitting unit comprising:
a main frame;
a support disposed on the main frame;
at least one of light sources disposed on a mounting region that is defined by a secured region secured to the support,
wherein the mounting region is tilted at an angle between −65 to −50 degrees with respect to the support toward a corner of the main frame and configured to deliver light toward a corner region of the main frame, and wherein the at least one of light sources is controlled to emit a light an intensity greater than or equal to a minimum intensity required for a sterilization.

2. The light emitting unit according to claim 1, wherein the support is formed without a circuit pattern.

3. The light emitting unit according to claim 1, wherein the support has an elongated shape in a first direction.

4. The light emitting unit according to claim 3, wherein the secured region extends to a second direction different from the first direction.

5. The light emitting unit according to claim 4, wherein the mounting region is tilted to a third direction different from the first direction and the second direction.

6. The light emitting unit according to claim 5, wherein the light source is configured to emit a light toward the third direction different from the first direction and the second direction.

7. A light emitting unit comprising:
a support including a first secured region including a first mounting region and a second secured region including a second mounting region;
a first light source disposed on the first mounting region of the first secured region; and
a second light source disposed on the second mounting region of the second secured region,
wherein the support has an elongated shape,
wherein the second secured region is tilted at a predetermined angle in a different direction with respect to the first secured region, and
wherein at least one of the first light source or the second light source are controlled to satisfy a following equation:

$$T = D \times r^2 \times 1/\alpha \times 1/P0$$

wherein T is a time of sterilization, D is a dose of light delivered per unit surface area of a target by at least one of the first light source or the second light source, r is a distance to the target, α is an experimental contestant, and P0 is a light power of the first light source or the second light source.

8. The light emitting unit according to claim 7, wherein the first light source and the second light source have different light exit surfaces from each other.

9. The light emitting unit according to claim 8, wherein the first light source is configured to deliver a first light along a first direction.

10. The light emitting unit according to claim 9, wherein the second light source is configured to deliver a second light along a second direction that is different form the first direction.

11. The light emitting unit according to claim 8, wherein the first light source and the second light source are spaced apart from each other by a predetermined distance.

12. The light emitting unit according to claim 10, wherein the support extends in a third direction different from at least one of the first direction or the second direction.

13. A light emitting unit comprising:
a main body;
a first support and a second support that are supported by the main body;
a first secured region and a second secured region that are disposed on the first support and the second support, respectively;
a first light source disposed on a first mounting region of the first secured region; and
a second light source disposed on a second mounting region of the second secured region,
wherein the first light source is disposed on a lower surface of the first support and the second light source is disposed on a lower surface of the second support, and
wherein each of the first support and the second support are movable up and down with a region of each of the first support and the second support that is partially secured to the main body, and
wherein at least one of the first light source or the second light source are controlled to satisfy a following equation:

$$T = D \times r^2 \times 1/\alpha \times 1/P0$$

wherein T is a time of sterilization, D is a dose of light delivered per unit surface area of a target by at least one of the first light source or the second light source, r is a distance to the target, α is an experimental contestant, and P0 is a light power of the first light source or the second light source.

14. The light emitting unit according to claim 13, wherein the first light source and the second light source are configured to deliver light along directions including a lateral direction and a downward direction.

15. The light emitting unit according to claim 13, wherein the first light source and the second light source are configured to deliver light to different angles from each other.

16. The light emitting unit according to claim 13 wherein at least one of the first support or the second support has an elongated shape and is disposed side by side with the main body.

17. The light emitting unit according to claim 13, wherein at least one of the first support or the second support has a longitudinal end.

18. The light emitting unit according to claim 13, wherein at least one of the first mounting region or the second mounting region is bendable.

19. The light emitting unit according to claim 13, wherein at least one of the first light source or the second light source is configured to deliver light in an angle that depends on a bending angle defined by the first support and the second support.

20. The light emitting unit according to claim 19, wherein the bending angle of opposite ends of each of the first support and the second support is adjusted based on a sterilization area sterilized by at least one of the first light source or the second light source.

* * * * *